(12) United States Patent
Zhang et al.

(10) Patent No.: US 7,103,250 B1
(45) Date of Patent: Sep. 5, 2006

(54) OPTICAL FIBER WITH HIGH SMALL-ANGLE SCATTER AND SENSOR USING SAME

(75) Inventors: Lu Zhang, Painted Post, NY (US); Daniel Aloysius Nolan, Corning, NY (US); Snigdharaj Kumar Mishra, Wilmington, NC (US); Alexej Sysoliatin, Moscow (RU)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 11/294,224

(22) Filed: Dec. 2, 2005

(51) Int. Cl.
*G02B 6/26* (2006.01)
*G02B 6/42* (2006.01)
*G02B 6/02* (2006.01)

(52) U.S. Cl. .......................... 385/123; 385/27; 385/28; 385/30

(58) Field of Classification Search .................. 385/5, 385/27–30, 122
See application file for complete search history.

(56) References Cited

U.S. PATENT DOCUMENTS

2003/0174516 A1* 9/2003 Goto et al. .................. 362/551

OTHER PUBLICATIONS

Eric G. Rawson; "Analysis of Scattering from Fiber Waveguides with Irregular Core Surfaces"; Applied Optics, vol. 13, No. 10, pp. 2370-2377, Oct. 1974.*

* cited by examiner

*Primary Examiner*—Michelle Connelly-Cushwa
*Assistant Examiner*—Chris Chu
(74) *Attorney, Agent, or Firm*—Suetlana Z. Short (57) ABSTRACT

An optical fiber (10) having a first section (10A) with little or no small-angle scattering (SAS) and a second section (10B) with an increased amount of SAS is disclosed. The optical fiber is formed by changing the draw temperature ($T_D$) and/or the draw speed ($V_D$) so as to induce index of refraction perturbations (P) at a core interface (40). The SAS optical fiber is useful in forming an evanescent optical fiber sensor (400), wherein the increased SAS enhances an evanescent wave portion (436) of a guided wave (434), which leads to increased sensitivity when measuring a property of a test medium (500).

16 Claims, 8 Drawing Sheets

OPTICAL FIBER WITH HIGH SMALL-ANGLE SCATTER AND SENSOR USING SAME

BACKGROUND OF THE INVENTION

1. Field of the Invention

The present invention relates generally to optical fibers, and particularly to optical fibers having a relatively large amount of small-angle scatter, and sensors using same.

2. Technical Background

Optical fibers were developed some thirty years ago for long-distance telecommunication because of their large bandwidth, light weight, immunity from electromagnetic interference, and other advantageous properties. The typical optical fiber has a high-refractive-index core region surrounded by a low-refractive-index cladding. A protective coating is usually provided over the cladding to protect the structure from the environment. Light injected into the optical fiber travels down the core region of the optical fiber, with a small portion of the light propagating in the cladding as an evanescent field ("evanescent wave"). The evanescent wave typically penetrates a short distance into the cladding (e.g., a few microns), depending on the optical fiber's refractive index profile.

The distance over which optical signals can be transmitted over an optical fiber is limited by attenuation (loss) due to absorption and scattering (e.g., Rayleigh, Brillouin and weak scattering), as well as from geometric effects (e.g., bending). Consequently, over the years, tremendous effort has been directed to studying and reducing these sources of signal attenuation.

More recently, optical fibers have been used in sensors for measuring a host of different physical properties such as temperature, pressure, strain, chemical composition, current/voltage, vibration/acceleration, and absorbance/fluorescence. One type of optical fiber sensor is referred to as an "evanescent optical fiber sensor." In a typical evanescent optical fiber sensor, light from the optical fiber core is transferred to the test medium via optical coupling of the evanescent wave with the test medium. The change in the amount and/or wavelength of the detected light is then translated into a measurement of the test medium.

Typically, the sensitivity of an evanescent optical fiber sensor is improved by transferring more light from the core to the test medium beyond that naturally conveyed by the evanescent wave. For example, increasing the strength of the evanescent wave penetrating into a biological sample to be assayed increases the amount of fluorescence, which translates into improved sensor performance. The need for improved evanescent optical fiber sensors is growing due to the increasing demand for measurement sensitivity.

SUMMARY OF THE INVENTION

One aspect of the invention is a method of forming an optical fiber. The method includes utilizing an optical fiber preform adapted to form a refractive index profile having a core interface when the preform is drawn into an optical fiber. The method also includes drawing an optical fiber from the preform at a first draw temperature and a first draw speed to form a first optical fiber section having a first amount of small-angle scattering (SAS). The method further includes changing at least one of the first draw temperature and the first draw speed so as to form a second optical fiber section contiguous with the first optical fiber section. The second optical fiber section has a second amount of small-angle scattering (SAS) at the core interface that is greater than the first amount of SAS in the first optical fiber section.

In another aspect, the present invention includes an optical fiber. The optical fiber has a core, a cladding and a core interface. The optical fiber includes first and second contiguous optical fiber sections. The first optical fiber section has a first amount of small-angle scattering (SAS) at the core interface and the second optical fiber section has a second amount of SAS at the core interface. The second amount of SAS is preferably greater than the first amount of SAS.

In another aspect, the present invention includes an optical fiber sensor apparatus for measuring a property of a test medium. The optical fiber sensor includes a first optical fiber section having an input end and a first amount of small-angle scattering (SAS). A second optical fiber section is optically coupled to the first optical fiber section and has a second amount of SAS that is greater than the first amount of SAS. The second optical fiber section is evanescently coupled to the test medium. A photodetector unit is optically coupled to the output end of the second optical fiber and is adapted to measure variations in light output from the output end due to light propagating in the second optical fiber section and interacting with the test medium. The measured variations in light output are used to deduce one or more properties of the test medium.

Additional features and advantages of the invention will be set forth in the following detailed description, and in part will be readily apparent to those skilled in the art from that description or recognized by practicing the invention as described herein, including the following detailed description, claims, as well as appended drawings.

It is to be understood that both the foregoing general description and the following detailed description are present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description, serve to explain the principles and operations of the invention.

DETAILED DESCRIPTION OF THE PREFERRED EMBODIMENTS

Reference will now be made in detail to the preferred embodiments of the invention, examples of which are illustrated in the accompanying drawings. Whenever possible, the same reference numerals are used throughout the drawings to refer to the same or like parts.

Figure 1:
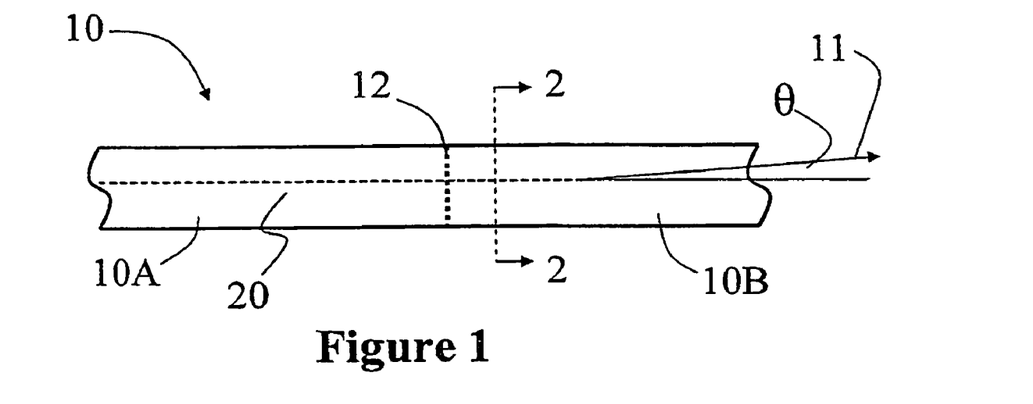
FIG. 1 is a side view of an example embodiment of a portion of the small-angle scattering (SAS) optical fiber according to the present invention.

FIG. 1 is a side view of a portion of an example embodiment of SAS optical fiber 10 according to the present invention. SAS optical fiber 10 includes two sections: a first optical fiber section 10A having a first amount (SAS1) of SAS, and a second optical fiber section 10B formed integral with the first optical fiber section and having a second amount (SAS2) of SAS, wherein SAS1<SAS2. The term "small-angle scatter" as used herein and abbreviated as "SAS," refers to the forward scattering of light within a relatively narrow angular cone θ (e.g., 0 to 10°) relative to the original direction of propagation, as illustrated by arrow 11 in FIG. 1. In an example embodiment, SAS1 is much smaller than SAS2, i.e., by a factor of 100× or more (e.g., 100× to 1000×). The amount of SAS supported by optical fiber 10 as compared to the corresponding low-loss optical fiber is discussed in detail below.

A boundary 12 is shown as a dashed line between the two optical fiber sections 10A and 10B. In practice, boundary 12 represents a distance (e.g., a centimeter or so) over which the transition from first optical fiber section 10A to second optical fiber section 10B occurs.

Figure 2:
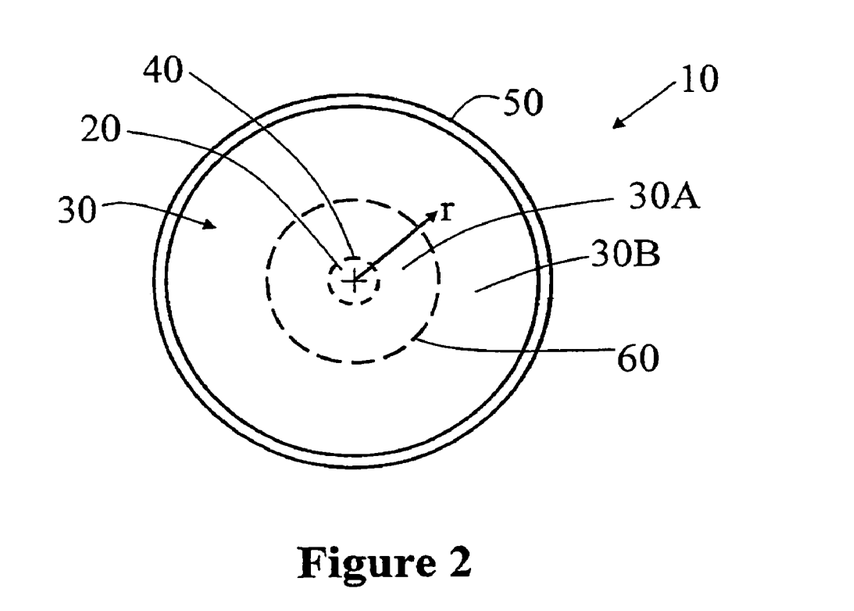
FIG. 2 is cross-sectional view of the example SAS optical fiber of FIG. 1, taken along the line 2—2, and illustrating the core interface along with a cladding interface defined by two cladding layers having different refractive indices.
Figure 5:
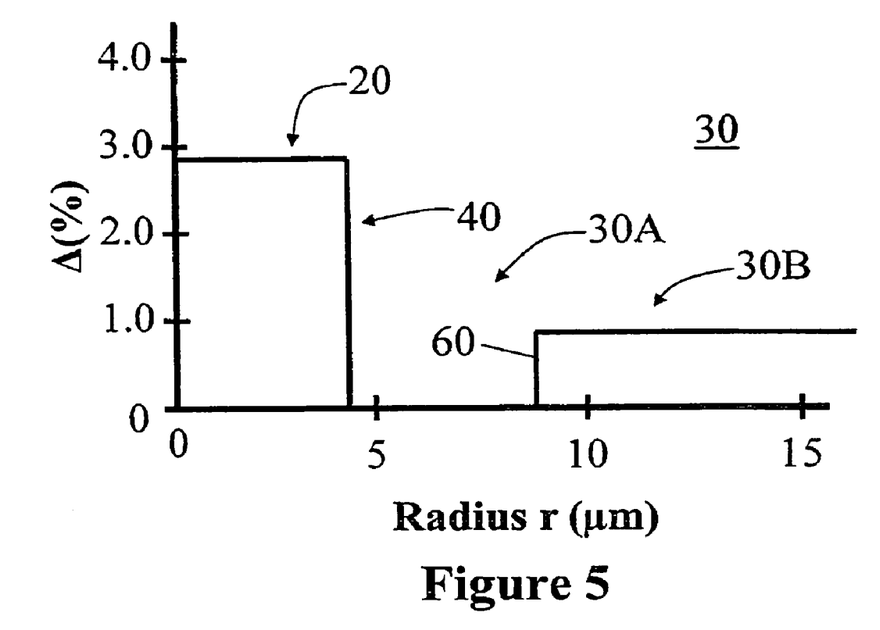
FIG. 5 is a plot of a refractive index delta profile $\Delta(\%)$ as a function of fiber radius r ($\mu$m) for the optical fiber associated with the plot of FIG. 4.

FIG. 2 is a cross-sectional view of second section 10B of SAS optical fiber 10 as taken along the line 2—2 in FIG. 1. Optical fiber 10 has a core region ("core") 20 surrounded by a cladding region ("cladding") 30, thereby defining a (cladding) core interface 40. In the present invention, the term "interface" refers to a location where the index of refraction changes abruptly. In an example embodiment, a protective outer coating 50 covers cladding 30. As shown in FIG. 5, (discussed below), in an example embodiment, the core of optical fiber 10 has a step refractive index profile and refractive index, which corresponds to the refractive index delta (Δ%) given by $\Delta(\%) = [(n(r)^2 - n_0^2)/2n(r)^2] \times 100$, where r is the radial coordinate measured from the optical fiber center, n(r) is the refractive index at a radial distance r from the optical fiber center, and $n_0$ is the outermost cladding refractive index.

In the discussion below, particular portions of the refractive index delta profile at a given distance r are said to have a refractive index delta of Δ(%). In an example embodiment of the present invention, optical fiber section 10B has a core refractive index delta Δ(%)≧2%, while in a more specific example embodiment, the core refractive index delta Δ(%) satisfies the relationship $$2 \leq \Delta(\%) \leq 5.$$

In an example embodiment illustrated in FIG. 2, cladding 30 includes a first cladding layer 30A and a second cladding layer 30B having different indices of refraction that define a cladding interface 60. Cladding 30 can include additional cladding layers, etc., that in turn define additional cladding interfaces 60. In another example embodiment illustrated below in connection with the example refractive index profiles of Examples 3, 4 and 5, discussed below, the refractive index profile includes an annular silica core 20 that surrounds a lower-index internal region 22, thereby defining core interfaces 40 on respective sides of the annular core.

Figure 3:
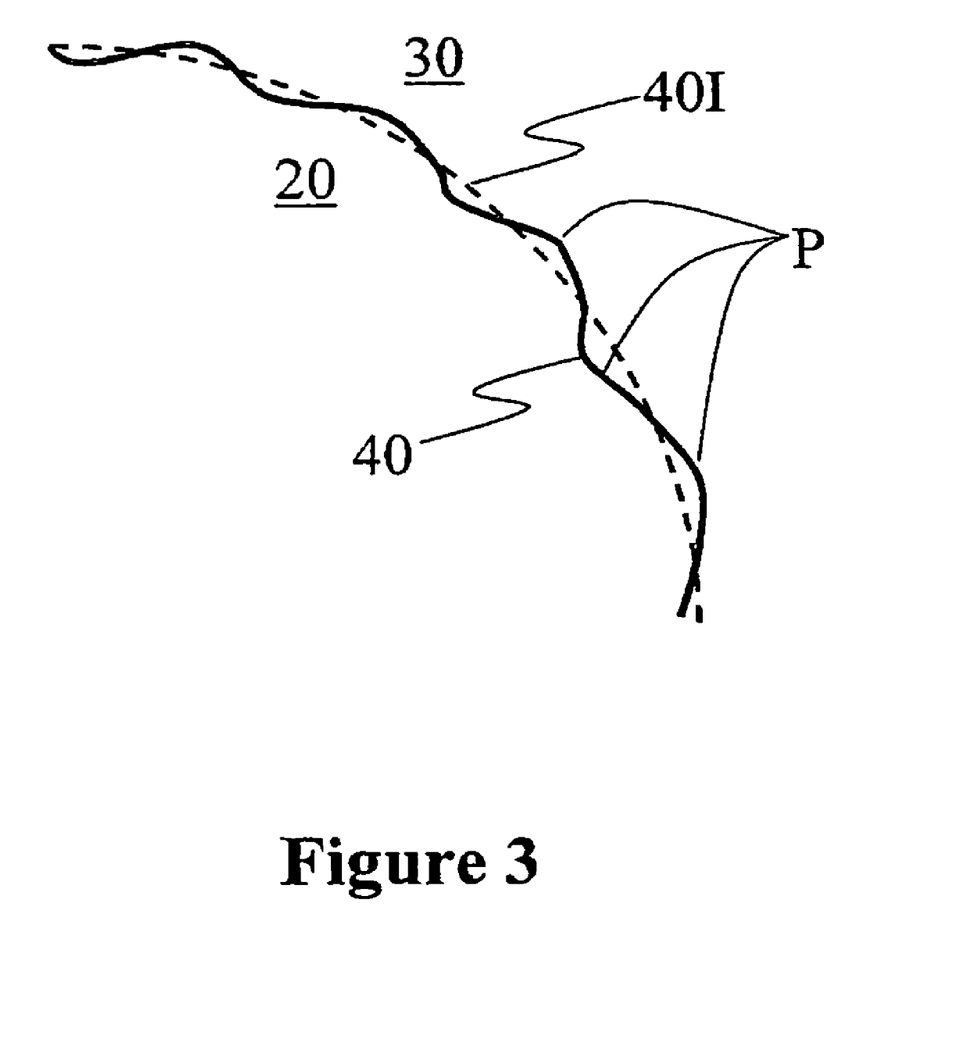
FIG. 3 is a close-up view of the core interface of shown in FIG. 2, illustrating the refractive index perturbations that lead to enhanced SAS in the second optical fiber section.

FIG. 3 is a close-up view of core interface 40 shown in FIG. 2. A conventional low-loss optical fiber has a relatively smooth core interface, as illustrated by an idealized core interface 40I, shown as a dashed line for the sake of reference. Idealized core interface 40I represents, for example, the core interface of first optical fiber section 10A, which has a small or insignificant amount SAS1 of SAS. However, the core interface 40 of optical fiber section 10B has an irregular shape intentionally formed so as to vary from the ideal smooth interface 40I. This is accomplished by using the fabrication methods of the present invention as described in detail below. The variations in core interface 40 are represented as random perturbations P in the refractive index profile. The perturbations P lead to an increased (enhanced) amount of SAS relative to ideal core interface 40I. It should be noted that the perturbations P also vary along the length of the optical fiber.

Refractive index perturbations P can be formed at any interface, such as one or more cladding interfaces 60, as well as one or more core interfaces 40. In some cases, the strength of the evanescent wave at these interfaces is small or negligible so that the amount of SAS generated these interfaces also tends to be small or negligible. On the other hand, the inventors discovered that a refractive index profile with interfaces in addition to just a single core interface 40 enhances the creation of refractive index perturbations P at the core interface. The inventors believe that an additional interface in the optical fiber creates a viscosity mismatch when the optical fiber is drawn. This increases the amount of stress at (first) core interface 40, which in turn facilitates the creation of refractive index perturbations P.

Figure 4:
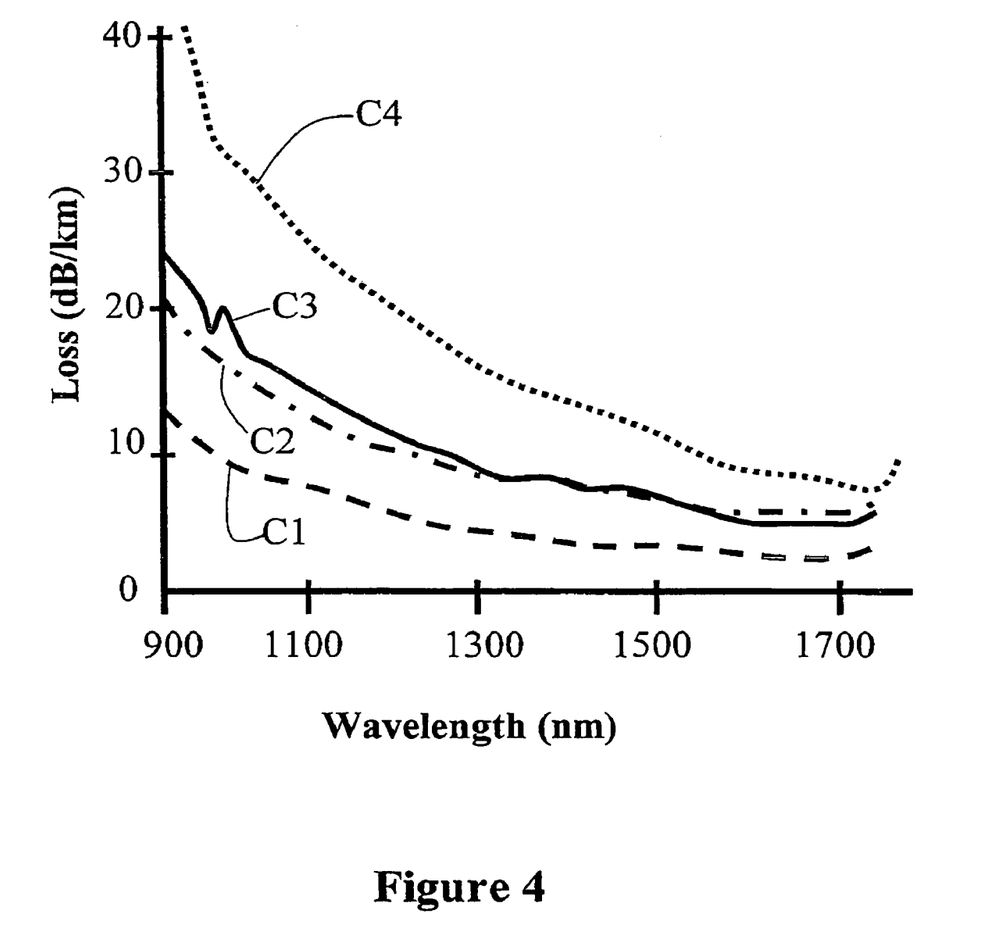
FIG. 4 is a plot, based on experimental data, of the loss (dB/km) vs. wavelength (nanometers, m) due to SAS for an optical fiber having a step refractive index profile with a Germanium-doped $SiO_2$ core and fluorine-doped silica in a cladding, illustrating how the SAS is affected by changing the draw temperature and draw velocity when forming the optical fiber.

The amount SAS2 of SAS in section 10B of optical fiber 10 depends on the particular refractive index delta profile Δ(%), the draw temperature $T_D$ and the draw speed $V_D$ used when making the optical fiber. FIG. 4 is a schematic plot based on experimental data of the loss (in dB/km) vs. wavelength (in nm) for an example optical fiber having the step refractive index profile as shown in FIG. 5. In the optical fiber of FIG. 4, core 20 is formed from Germania-doped $SiO_2$, the first cladding layer 30A is formed from fluorine-doped silica, and the second cladding layer 30B is formed from silica. Core 20 has a core refractive index delta Δ(%)=2.8.

FIG. 4 is a plot of the loss in dB/km due to SAS versus wavelength (nm) for an optical fiber 10 formed at different draw temperatures $T_D$ and draw speeds $V_D$, illustrating the effect of draw temperature and draw speed on the creation of SAS. Curve C1 corresponds to a draw temperature $T_D=1880°$ and a draw speed $V_D=60$ m/min, and exhibits the smallest amount of SAS. Curve C1 thus represents example conditions for forming optical fiber section 10A, which has a relatively small amount SAS1 of SAS. Curve C2 corresponds to a draw temperature $T_D=1880°$ and a draw speed $V_D=30$ m/min, and exhibits an increased amount of SAS as compared to curve C1 (about 2 dB/km at 1550 nm and about 3 dB/km at 1100 nm). Curve C3 corresponds to a draw temperature of $T_D=1940°$ and a draw speed $V_D=60$ m/min, and exhibits slightly increased SAS at wavelengths below about 1350 nm as compared to curve C2. Curve C4 corresponds to a draw temperature of $T_D=1940°$ and a draw speed $V_D=30$ m/min, and exhibits a significant increase in SAS as compared to curves C1, C2 and C3 (e.g., about 10 dB/km at 1550 nm and about 20 dB/km at 1100 nm as compared to curve C1). Curve C4 is notable in that it confirms that an increase in draw temperature $T_D$ combined with a decrease in draw speed $V_D$ is effective in significantly increasing the amount of SAS (about 3 dB/km at 1550 nm and about 5 dB/km at 1100 nm) in an otherwise low-SAS optical fiber (i.e., curve C1).

In an example embodiment of the present invention, the draw temperature $T_D$ ranges from 1800 C. to 2100° C., and in a more specific embodiment, ranges from 1940° C. to 2000° C. Likewise, in an example embodiment of the present invention, the draw speed $V_D$ ranges from 10 meters/min to 60 meters/min, and in a more specific embodiment, ranges from 10 meters/min to 20 meters/min.

The relatively high core refractive index delta (e.g., $\Delta(\%) \geq 2$) of optical fiber 10 of the present invention allows for refractive index perturbations P to generate noticeable amounts of SAS. Further, the amount of SAS depends upon the particular refractive index profile used for the optical fiber. Thus, in one example embodiment, the amount of SAS is 1.5× or greater than that of the corresponding low-loss optical fiber. In another example embodiment, the amount of SAS is greater than 1.5× as compared to the corresponding low-loss optical fiber. In other exemplary embodiments, the amount of SAS is between 1.5× and 1000× as compared to the corresponding low-loss optical fiber. In a same exemplary embodiment, the amount of SAS is between 1.5× and 100× as compared to the corresponding low-loss optical fiber. In yet other embodiments, the amount of SAS is between 1.5× and 16× as compared to the corresponding low-loss optical fiber.

In an example embodiment, single-mode optical fibers 10 have a refractive index delta profile with a core refractive index delta of $\Delta(\%)<2$. However, such optical fibers are generally not preferred because of the relatively large radial extent of the core. Such profiles are formed by extending the core-cladding region radially outward as compared to an optical fiber having a relatively high refractive index profile.

Example Refractive Index Profiles

Five example refractive index profiles of SAS optical fiber 10 are set forth below for the sake of illustration. Each of the example refractive index profiles is designed to support enhanced SAS using the methods described in detail below. The example refractive index profiles and the calculations for the relative amounts of SAS were derived via computer modeling based on the treatment of SAS in optical fibers as set forth in an article by Eric R. Rawson, entitled "Analysis of scattering from fiber waveguides with irregular core surfaces," *Applied Optics* Vol. 13, No. 10, page 2370 (October 1974). In the example profiles below, the various parts of the optical fiber such as the core, the cladding and the core and cladding interfaces are labeled for the sake of reference.

EXAMPLE 1

Figure 6:
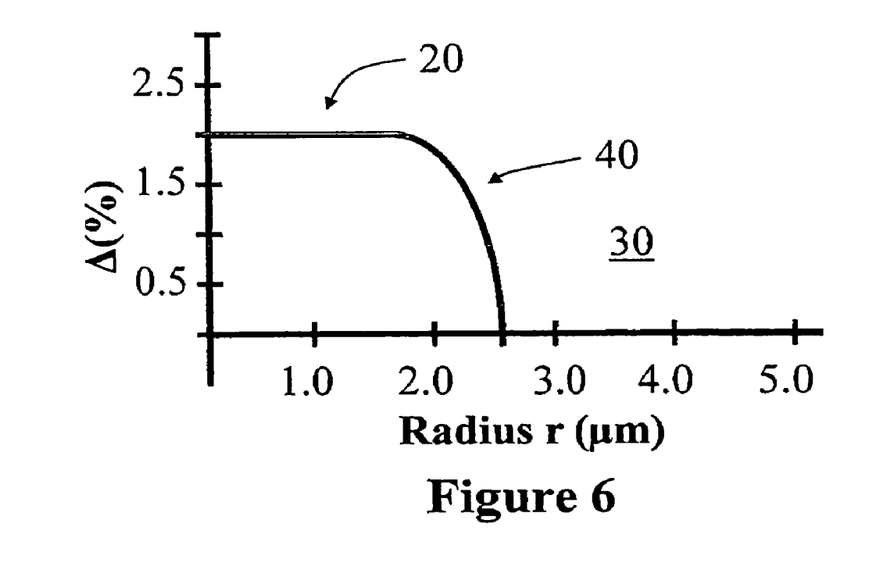
FIG. 6 is a plot of a refractive index delta profile Δ(%) as a function of fiber radius r (μm) for a first example embodiment of an SAS optical fiber according to the present invention.

FIG. 6 is a plot of the refractive index delta profile $\Delta(\%)$ as a function of fiber radius r (μm) for a first example embodiment of SAS optical fiber 10. Optical fiber 10 is single mode at a wavelength of 1.55 μm. The refractive index profile has a substantially a step refractive index profile with a core delta of $\Delta(\%)=2.0$ that tapers downward toward zero at a radius r=1.75 μm, reaching zero at a radius r=2.5 μm. Model calculations indicate that an optical fiber 10 with the refractive index profile of FIG. 6 can support SAS of approximately 43× as compared to the corresponding low-loss version of the optical fiber.

EXAMPLE 2

Figure 7:
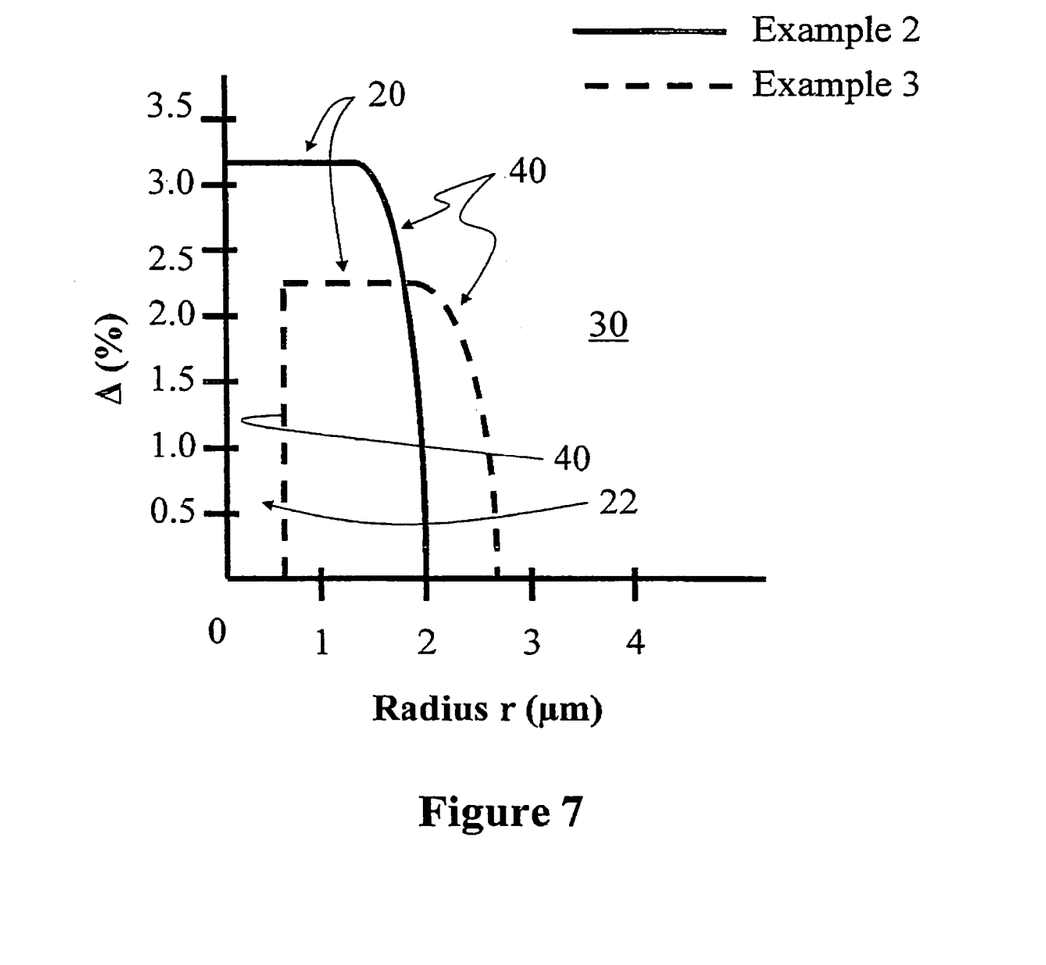
FIG. 7 is a plot of a refractive index delta profile Δ(%) as a function of fiber radius r (μm) for second and third example embodiments of an SAS optical fiber according to the present invention

FIG. 7 includes a plot of the refractive index profile $\Delta(\%)$ as a function of fiber radius r (μm) for a second example embodiment of SAS optical fiber 10, as indicated by the solid line. Optical fiber 10 is single mode at a wavelength of 1.55 μm. The refractive index profile of FIG. 7 is similar to that of FIG. 6, but has a higher core refractive index delta of $\Delta(\%)=3.2$ that tapers downward toward zero at a radius r=1.3 μm, reaching zero at a radius r=2.0 μm. Model calculations indicate that an optical fiber 10 with the refractive index profile of FIG. 7 can support SAS of approximately 73 times larger as compared to the corresponding low-loss version of the optical fiber

EXAMPLE 3

FIG. 7 also includes a plot of the refractive index profile delta $\Delta(\%)$ as a function of fiber radius r (μm) for a third example embodiment of SAS optical fiber 10, as indicated by the dashed line. Optical fiber 10 is single mode at a wavelength of 1.55 μm. The refractive index profile has an annular core with a substantially step refractive index that extends from about r=0.7 μm to about r=2.7 μm. The core has a refractive index delta of $\Delta(\%)=2.5$ that tapers downward toward zero at a radius r=2.7 μm. The central region 22 has a refractive index delta $\Delta(\%)=0$. The annular shape of core 20 allows the evanescent wave to interact with both core interfaces 40.

Figure 8:
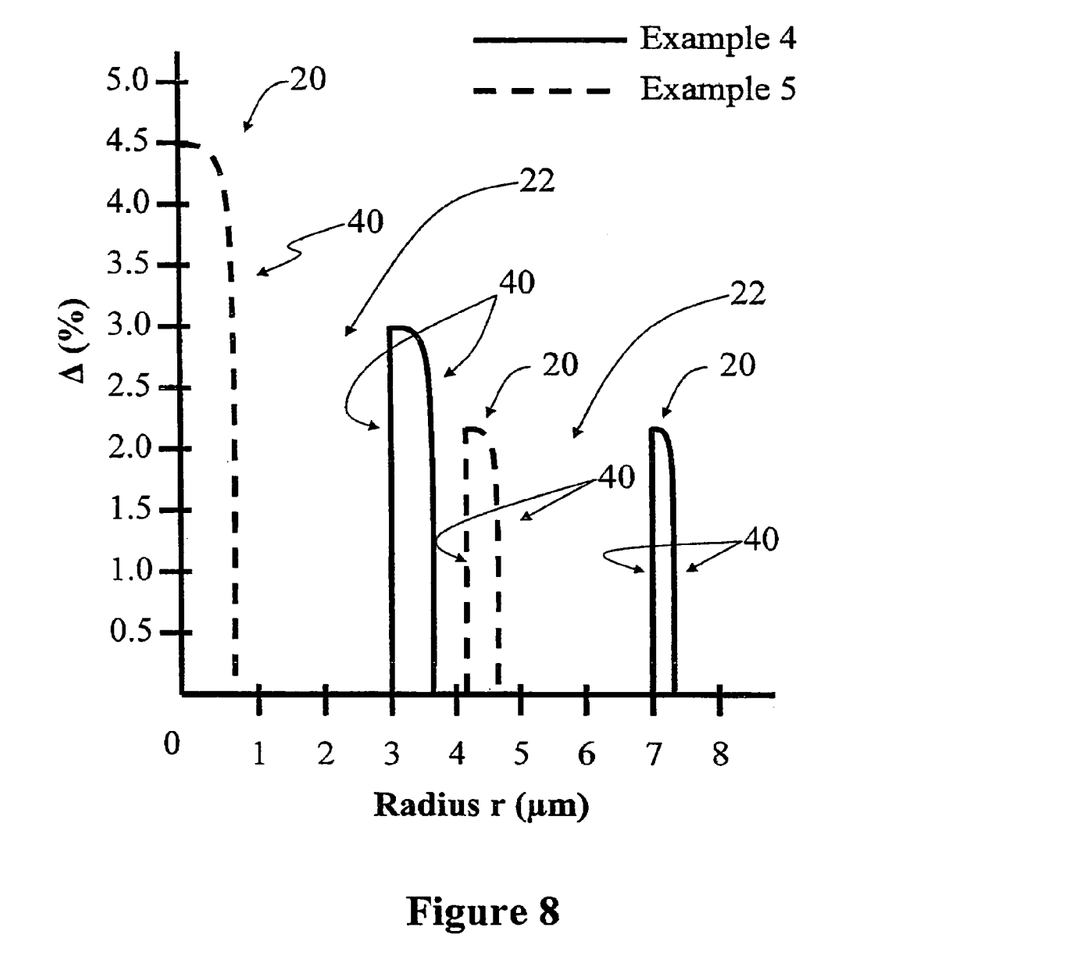
FIG. 8 is a plot of a refractive index delta profile Δ(%) as a function of fiber radius r (μm) for fourth and fifth example embodiments of an SAS optical fiber according to the present invention.

Model calculations indicate that an optical fiber 10 with the refractive index profile of FIG. 8 can support SAS of approximately 15 times larger than the corresponding low-loss version of the optical fiber.

EXAMPLE 4

FIG. 8 is a plot of the refractive index profile $\Delta(\%)$ as a function of fiber radius r (μm) for a fourth example embodiment of SAS optical fiber 10, as indicated by the solid line. Optical fiber 10 is single mode at a wavelength of 1.55 μm. The refractive index profile has two substantially step-index annular cores. The first annular core extends from about r=3 μm to about r=3.6 μm and has a core refractive index delta of $\Delta(\%)=3$. The second annular core extends from about r=μm to about r=7.4 μm and has a core refractive delta index delta of $\Delta(\%)=2.2$. Cladding 30 surrounds the two annular cores 20 and has a cladding refractive index of $\Delta(\%)=0$. The annular cores 20 allows for the guided wave to interact with a total of four core interfaces 40.

Figure 9:
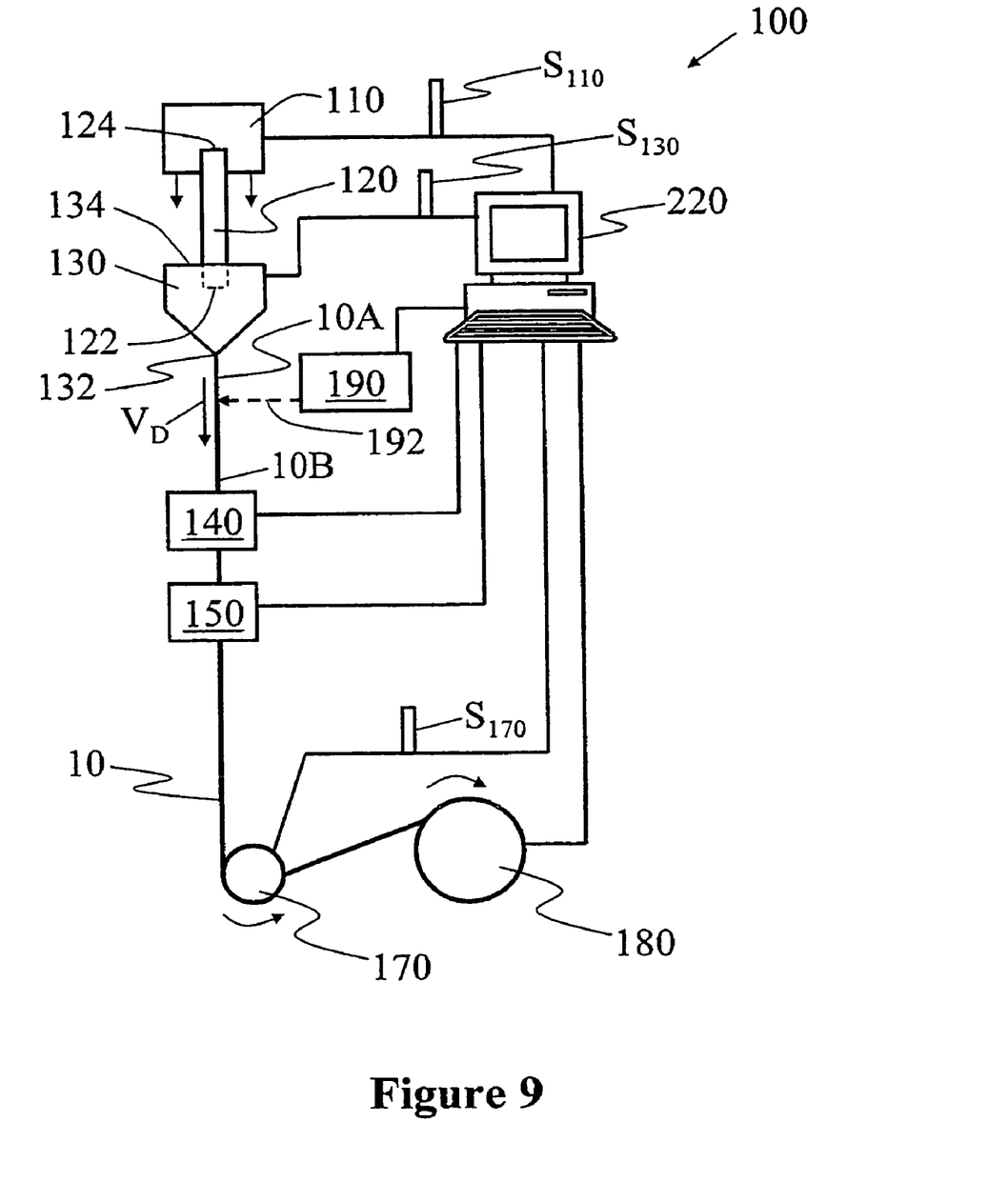
FIG. 9 is a schematic diagram of an example embodiment of a fiber drawing apparatus used for fabricating the SAS optical fiber of the present invention.

Model calculations indicate that an optical fiber 10 with the refractive index delta profile of FIG. 9 can support SAS of approximately ($4.5\times10^4$) higher as compared to the corresponding low-loss version of the optical fiber

EXAMPLE 5

FIG. 8 also includes a plot of the refractive index delta profile $\Delta(\%)$ as a function of fiber radius r (μm) for a fifth example embodiment of SAS optical fiber 10, as indicated by the dashed line. Optical fiber 10 is single mode at a wavelength of 1.55 μm. The refractive index profile has two substantially step-index cores 20; a solid central core and a surrounding annular core. The central core extends out to a radius of about r=0.7 μm and has a core refractive index delta of $\Delta(\%)$=4.5. The annular core extends from about r=4.2 μm to about r=4.6 μm and has a core refractive index delta of $\Delta(\%)$=2.2. Cladding 30 has a cladding refractive index profile delta value $\Delta(\%)$=0. The combination of a central core and a surrounding annular core allows for the guided wave to interact with three core interfaces 40.

Figure 10:
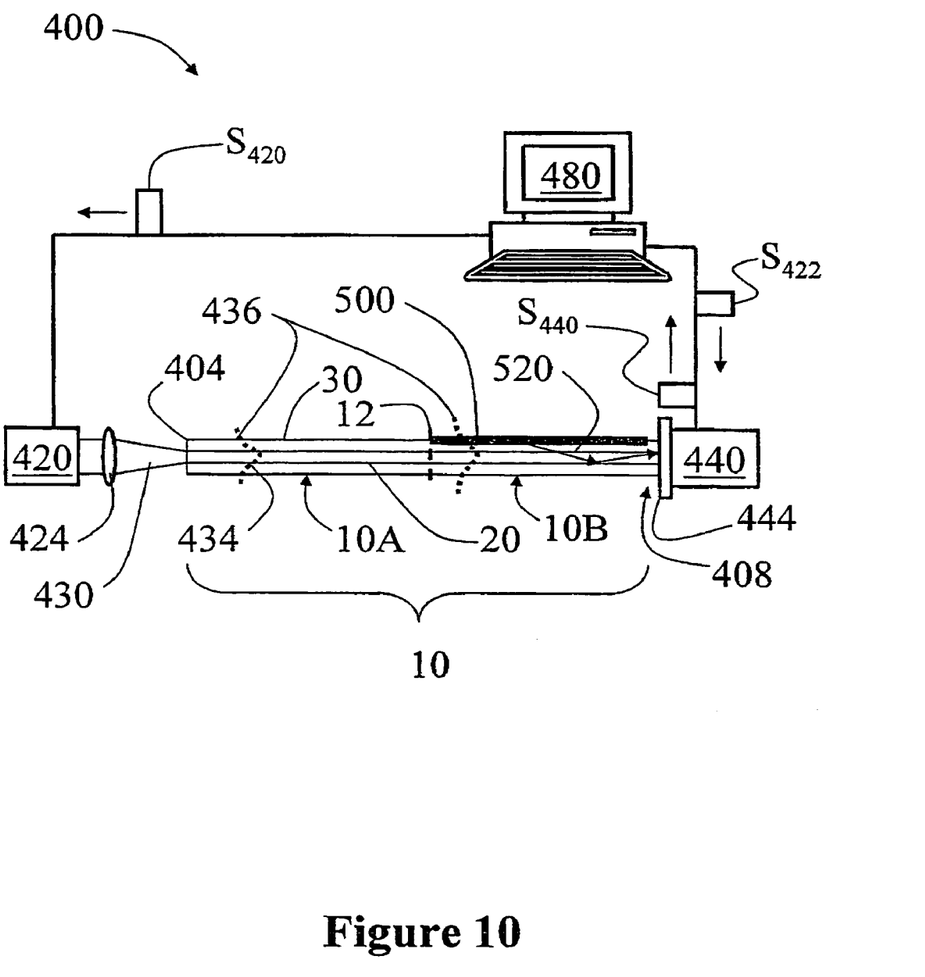
FIG. 10 is schematic diagram of an example embodiment of an optical sensor according to the present invention for measuring a property of a test medium.

Model calculations indicate that an optical fiber 10 with the refractive index profile of FIG. 10 can support SAS of approximately $10^3$ higher magnitude as compared to the corresponding low-loss version of the optical fiber.

Method of Fabricating the SAS Optical Fiber

FIG. 9 is an example embodiment of an optical fiber manufacturing apparatus 100 suitable for fabricating the SAS optical fiber of the present invention. Apparatus 100 includes a feed mechanism 110 that operably engages a preform 120 having a leading end 122 and a trailing end 124. Preform 120 is formed to yield a refractive index profile when drawn, such as the profiles discussed above in connection with Examples 1 through 8. In an example embodiment, preform 120 is formed using a vapor deposition process, such as modified chemical vapor deposition MCVD, plasma chemical vapor deposition (PCVD), vapor-phase axial deposition (VAD), or a like process.

Apparatus 100 includes a furnace 130 having an output end 132, and a receiving end 134 arranged to receive preform leading end 122 when the feed mechanism is activated. Downstream of furnace 130 is a measuring unit 140 (e.g., a laser micrometer), followed by a coating applicator unit 150, which optionally applies and then cures a coating 50 (FIG. 2) onto the optical fiber, if desired. A pinch wheel 170 is arranged downstream of coating applicator unit 150 and is arranged to create tension in optical fiber 10 as the optical fiber is drawn. Pinch wheel 170 is also arranged to feed the optical fiber to a take-up spool 180.

Apparatus 100 also includes a heating unit 190 arranged adjacent to furnace output end 132 so as to be in thermal communication with optical fiber 10 via (heating) radiation 192 as the optical fiber is being drawn from the furnace output end 132. In an example embodiment, heating unit 190 includes a laser such as a $CO_2$ laser that emits radiation 192 at a wavelength 10.6 μm. Apparatus 100 further includes a controller 220 operably connected to feed mechanism 110, furnace 130, measuring unit 140, coating applicator 150, pinch wheel 170, take-up spool 180 and heating unit 190.

In accordance with the invention, and with reference to apparatus 100 of FIG. 9, the method of fabricating SAS optical fiber 10 includes a number of steps. The first step involves fabricating preform 120 so that it generates a desired refractive index profile when drawn into optical fiber 10. In particular, preform 120 is formed so as to generate a step refractive index profile having core interface 40 capable of supporting refractive index perturbations P sufficient to cause a desired amount of SAS, as discussed above.

In the next step, preform 120 is placed in apparatus 100 so that trailing end 124 is engaged by feed mechanism 110. In response to a control signal $S_{110}$ from controller 220, feed mechanism 110 introduces preform leading edge 122 into receiving end 134 of furnace 130. Furnace 130 has a draw temperature $T_D$ (e.g., on the order of 1900° C.), which is tightly controlled by controller 220 via a furnace control signal $S_{130}$. Furnace 130 acts to soften preform leading edge 122, which is then drawn out of furnace output end 132 at a given draw speed $V_D$ as newly formed first section 10A of optical fiber 10.

In forming optical fiber section 10A, the draw temperature $T_D$ and draw speed $V_D$ are selected and controlled by controller 220 to ensure that the amount SAS1 of SAS is small or minimal. In particular, the draw speed $V_D$ is controlled by the rotational speed of pinch wheel 170 via a signal $S_{170}$ from controller 220. The draw speed $V_D$ is related to the amount of tension applied to optical fiber 10, and thus relates to the amount of strain placed on the optical fiber as it is being drawn.

In forming optical fiber section 10B, the draw temperature $T_D$ and/or the draw speed $V_D$ is/are changed from that associated with forming optical fiber section 10B so as to create a larger amount SAS2 of SAS as compared to the amount SAS1 in optical fiber section 10A. In an example embodiment, the draw temperature $T_D$ is changed by controller 220 changing furnace control signal $S_{130}$. In another example embodiment, the draw temperature $T_D$ is increased by controller 220 sending a signal $S_{190}$ to heating unit 190 that causes the heating unit to emit heat radiation 192 (e.g., an infra-red laser beam) to optical fiber 10 as it exits output end 132 of furnace 130. A change in the draw speed $V_D$ is accomplished, for example, by controller 220 changing the rotational speed of pinch wheel 170 via control signal $S_{170}$.

Newly formed optical fiber sections 10A and 10B are measured by measuring unit 140 as the optical fiber exits furnace 130 to ensure the fiber has the proper dimensions. Optical fiber 10 then optionally proceeds through coating applicator 150, which coats the optical fiber with a UV-sensitive coating, and is stored on take-up spool 180. In an example embodiment, optical fiber 10 is formed with alternating optical fiber sections 10A–10B–10A–10B, etc.

Optical Fiber Sensor

FIG. 10 is a schematic diagram of an example embodiment of an optical fiber sensor 400 that utilizes the SAS optical fiber 10 according to the present invention. Optical fiber 10 as used in optical fiber sensor 400 has an input end 404 at optical fiber section 10A and an output end 408 at optical fiber 10B. In an example embodiment of apparatus 400, optical fiber section 10B is on the order of a meter or so.

Apparatus 400 also includes a light source 420 that emits light 430. In an example embodiment, light source 420 includes a laser or laser diode. In an example embodiment, light source 420 is adapted to generate different wavelengths of light 430, including visible light (e.g., 650 nm) and infra-red light (e.g., the C-band at 1550 nm). Light source 420 is optically coupled to first optical fiber section 10A at input end 404, e.g., via a focusing lens 424. Light 430, once coupled into optical fiber 10, travels down the optical fiber in the form of a lightwave 434 having an evanescent wave portion 436 that extends into cladding 30.

Apparatus 400 also includes a photodetector 440 optically coupled to output end 408 and arranged to receive light 430 output from optical fiber section 10B at output end 408. Photodetector 440 generates an electrical photodetector signal $S_{440}$ representative of the amount of light 430 received and detected. In an example embodiment, photodetector 440 is capable of detecting and processing different wavelengths of light. In an example embodiment, an optical filter 444 is arranged between optical fiber output end 408 and photodetector 440. Optical filter 444 is adapted to pass a fluorescent wavelength of the test medium and block the input wavelength(s) from light source 420.

Apparatus 400 also includes, in an example embodiment, a controller 480 operably coupled to light source 420 and to photodetector 440 for controlling the operation of the apparatus, and for storing information. Controller 480 includes processing electronics adapted to receive and process photodetector signal $S_{440}$ so as to output information concerning a given property of the test medium to be measured. In an example embodiment, controller 480 is a programmable computer such as a PC or workstation of the type commonly used to process data and control scientific apparatuses. In an example embodiment, controller 480 is adapted to perform evanescent spectroscopy based on photodetector signal $S_{440}$.

With continuing reference to FIG. 10, in the operation of apparatus 400, prior to making a measurement of a test medium, light source 420 and photodetector 440 are activated by controller 480 by an signals $S_{420}$ and a gating signal $S_{442}$, respectively, to obtain baseline and calibration measurements. In the absence of a test medium, lightwave 434 travels through section 10A, then through section 10B, and then out of output end 408, where the light is detected by photodetector 440. The only significant loss over this optical path is due to SAS in optical fiber section 10B.

Once these initial measurements are performed and the data stored in controller 480, a test medium 500 is arranged relative to optical fiber section 10B so as to be optically coupled thereto via evanescent wave portion 436. In one example embodiment, test medium 500 is supported directly by optical fiber section 10B, while in another example embodiment, optical fiber section 10B is immersed in the test medium. In another example embodiment, test medium 500 is embedded in cladding 30 so that it is closer to the core interface 40 than if it were arranged atop the cladding. Also in an example embodiment, if optical fiber 10 has a coating 50, this coating is removed from optical fiber section 10B so that test medium 500 can be placed so as to interact with evanescent wave portion 436.

Once test medium 500 is in place, light source 420 is again activated by controller 480 via signal $S_{420}$ to generate lightwave 434. Lightwave 434 propagates from optical fiber section 10A to optical fiber section 10B, where it encounters an increased amount of SAS. This causes some of the light in lightwave 434 to scatter at relatively small angles from the optical fiber into test medium 500. The effect of the increased amount of SAS in optical fiber section 10B is to increase the amount of light in evanescent wave portion 436. This in turn increases the amount of light that interacts with test medium 500, resulting in an enhanced measurement. The change in the amount and/or wavelength of light that exits output end 408 by virtue of the evanescent wave portion 436 interacting with the test medium is detected by photodetector 440, which is activated by gating signal $S_{442}$. The detected light is encoded in photodetector signal $S_{440}$, which is then processed by processing electronics in controller 480 to yield a measurement of a given property of test medium 500.

In an example embodiment, apparatus 400 is used to measure the presence or absence of a chemical species. In an example bio-sensor application, test medium 500 includes an absorbance- or fluorescence-indicator dye whose absorbance or fluorescence properties are changed by other elements (e.g., molecules) that make up the test medium.

Apparatus 400, according to an example embodiment, uses SAS optical fiber section 10B to excite fluorescence from surface-bound fluorophores and to couple the fluorescence, indicated schematically by light rays 520, back into the optical fiber, where it propagates and is detected by photodetector 440. Fluorescence 520 arises from species binding on the fiber surface resulting from the interaction (chemical, biochemical, bioaffinity, or immunogenic-type) of biomolecules (ligands) with their respective binding partners. The terms "ligand" and "binding partner" for the ligand are used to represent the two components in specific bioaffinity binding pairs, all of which are capable of recognizing and binding with the other partner in a biomolecular recognition pair. Examples of such binding pairs include: antigen-antibody, substrate-enzyme, effector-enzyme, inhibitor-enzyme, complementary nucleic acid strands (RNA or DNA), binding protein-vitamin, binding protein-nucleic acid, reactive dye-protein, reactive dye-nucleic acid, receptor-agonist or antagonist, and others.

Apparatus 400 can be used, for example, to detect the fluorescent wavelength of a biological test medium 500 to perform an efficient and selective immunoassay or hybridization assay. This may include, for example, biological recognition (binding) of an antigen by antibodies attached to the cladding of optical fiber section 10B with the attendant displacement of fluorescent-labeled antigens. The assay is performed by interacting biological test medium 500 with the evanescent wave 436, as described above, and measuring a change in amount of light detected by photodetector 440 at the fluorescence wavelength. In this example embodiment, controller 480 is programmed to process photodetector signals $S_{440}$ representative of changes in fluorescence and translate this information into the particular type of assay measurement.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed is:

1. A method of forming an optical fiber, comprising the steps of:
    utilizing an optical fiber preform adapted to form a refractive index profile having a core interface when the preform is drawn into an optical fiber;
    drawing an optical fiber from the preform at a first draw temperature and a first draw speed to form a first optical fiber section having a first amount of small-angle scattering (SAS); and
    changing at least one of the first draw temperature and the first draw speed so as to form a second optical fiber section contiguous with the first optical fiber section and having a second amount of small-angle scattering (SAS) at the core interface that is greater than the first amount of SAS in the first optical fiber section.

2. The method of claim 1, wherein changing the first draw temperature includes irradiating the optical fiber upon exiting an output end of a furnace.

3. The method of claim 1, including changing both the first draw temperature and the first draw speed.

4. The method of claim 1, wherein said changing at least one of the first draw speed and the first temperature is performed such that the second amount of SAS is increased relative to the first amount of SAS by a factor of 1.5× or greater.

5. The method of claim 1, wherein the second amount of SAS is increased relative to the first amount of SAS by a factor of between 1.5× and 1000×.

6. The method of claim 1, wherein the second amount of SAS is increased relative to the first amount of SAS by a factor of between 1.5× and 100×.

7. The method of claim 1, including forming the cladding to have two layers with different refractive indices so as to form a cladding interface that facilitates the formation of refractive index perturbations at the core interface so as to increase the second amount of SAS.

8. The method of claim 1, including forming the core as an annular core with a central region so as to define an internal core interface that supports the formation of refractive index perturbations in the second optical fiber section that creates additional SAS in the second optical fiber section.

9. The method of claim 1, including forming a core to have a refractive index of $\Delta(\%)$ such that $2 \leq \Delta(\%) \leq 5$.

10. An optical fiber having a core, a cladding and a core interface, comprising:
    a first optical fiber section having a first amount of small-angle scattering (SAS) at the core interface; and
    a second optical fiber section formed contiguous with the first section and having a second amount of SAS at the core interface, wherein the second amount of SAS is greater than the first amount of SAS.

11. The optical fiber of claim 10, wherein the second amount of SAS is greater than the first amount of SAS by a factor of 1.5× or greater.

12. The optical fiber of claim 10, wherein the second amount of SAS is greater than the first amount of SAS by a factor of between 1.5× and 1000×.

13. The optical fiber of claim 10, wherein the second amount of SAS is greater than the first amount of SAS by a factor of between 1.5× and 100×.

14. The optical fiber of claim 10, wherein the core has a refractive index of $\Delta(\%)$ such that $2 \leq \Delta(\%) \leq 5$.

15. The optical fiber of claim 10, wherein the cladding is made up of two layers having different refractive indices so as to form a secondary cladding interface that facilitates the formation of refractive index perturbations at the core interface so as to increase the second amount of SAS.

16. The optical fiber of claim 10, wherein the core is an annular core having a central region and an internal core interface that supports refractive index perturbations in the second optical fiber section that cause an additional amount of SAS in the second optical fiber section.

* * * * *